US008596383B2

(12) United States Patent
Montie et al.

(10) Patent No.: US 8,596,383 B2
(45) Date of Patent: Dec. 3, 2013

(54) METHOD FOR DETECTING HYDROCARBON ZONES IN A GEOLOGICAL FORMATION

(75) Inventors: Mark W. Montie, Dallas, TX (US); Charles L. Vavra, Lucas, TX (US)

(73) Assignee: Encana Oil & Gas (USA) Inc., Dallas, TX (US)

( * ) Notice: Subject to any disclaimer, the term of this patent is extended or adjusted under 35 U.S.C. 154(b) by 329 days.

(21) Appl. No.: 13/105,665

(22) Filed: May 11, 2011

(65) Prior Publication Data
US 2012/0285742 A1    Nov. 15, 2012

(51) Int. Cl.
*E21B 49/00*  (2006.01)
*E21B 47/00*  (2012.01)

(52) U.S. Cl.
USPC .......... 175/46; 175/50; 73/152.04; 73/152.23

(58) Field of Classification Search
USPC ................ 175/42, 46, 50; 73/152.04, 152.07, 73/152.09, 152.11, 152.23
See application file for complete search history.

(56) References Cited

U.S. PATENT DOCUMENTS

| | | | | |
|---|---|---|---|---|
| 2,213,904 A | * | 9/1940 | Dunn | 436/31 |
| 2,660,887 A | * | 12/1953 | Frei | 73/152.18 |
| 3,921,732 A | * | 11/1975 | Reynolds et al. | 175/50 |
| 7,308,139 B2 | | 12/2007 | Wentland et al. | |

* cited by examiner

*Primary Examiner* — Giovanna Wright
(74) *Attorney, Agent, or Firm* — Shaukat A. Karjeker; Colin C. Cahoon; Carstens & Cahoon, LLP

(57) ABSTRACT

A method for detecting hydrocarbon zones in a geological formation, including obtaining a plurality of pulverized drill cutting samples representative of the geological material encountered at measured depth intervals, each drill cutting obtained at periodic intervals during the drilling process; measuring each cutting sample with a color measuring device to obtain a value representing the degree of lightness of the particular cutting sample; and analyzing the measured lightness values by order of borehole depth that the respective cutting sample was obtained to determine the presence of geological zones likely to possess producible hydrocarbons. L* data may be combined with other well logging data to improve the hydrocarbon layer determination accuracy. A method also for locating the drill bit within a desired hydrocarbon layer during directional drilling.

15 Claims, 4 Drawing Sheets

METHOD FOR DETECTING HYDROCARBON ZONES IN A GEOLOGICAL FORMATION

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to systems and methods for processing geological data related to the shale layers penetrated during borehole drilling.

2. Description of Related Art Including Information Disclosed Under 37 CFR 1.97 and 1.98

When drilling wells in search of oil or gas, it is essential for oil exploration personnel to conduct a proper analysis of the geological formation to determine which drilling location is most likely to contain producible quantities of the desired hydrocarbon. This is especially important given the high initial and ongoing costs of drilling operations.

Exploratory wells are often drilled to determine if a particular horizon will be productive of minerals. When drilling such wells, a mud logger monitors and logs the drill cuttings and other parameters at regular intervals along the borehole depth. Often, the drilling bit is accompanied down the borehole by a tool that takes measurements of the geological structure of the hole as it is drilled. Such tools produce data that make up the electric logs or gamma-ray logs of the borehole, depending on the type of sensors present on the tool. It is from these electric logs or gamma-ray logs that attempts are made to map the strata and to determine the presence of hydrocarbon zones in the borehole and, hopefully, to indicate to the drilling company the location of the sought-after productive formations. However, such logs can be inaccurate and the tools can be costly and unreliable.

To improve the accuracy of analysis of the strata, it is possible to obtain core samples at specified depths within the borehole (called coring). When coring, a core bit is attached to the drill pipe and a column of rock is cut from the formation. This column of rock (the core) is then sent to a laboratory where it can be analyzed for the presence of oil and gas, and its other characteristics are determined. Once the core analysis is complete, it is possible to obtain a map of the geological structure of the borehole that is more accurate than electric or gamma-ray logging can produce. However, such a process, although highly accurate, is exceedingly costly and time consuming and is impractical to perform on a regular basis.

What is needed is a method for determining the presence of hydrocarbon layers within a borehole that is more accurate than traditional well logging methods, yet less costly and time consuming than coring. The present invention satisfies these needs and others, as demonstrated by the detailed discussion of the embodiments herein.

BRIEF SUMMARY OF THE INVENTION

A method for detecting hydrocarbon zones in a geological formation, the method steps comprising: obtaining a plurality of pulverized drill cutting samples, each drill cutting sample representative of the geological material encountered at a measured depth during the drilling of a borehole, with each drill cutting having been obtained at periodic intervals during the drilling process; measuring each pulverized drill cutting sample with a color measuring device to obtain a value representing the degree of lightness of the particular pulverized drill cutting sample; and analyzing the measured lightness values by order of borehole depth that the respective pulverized drill cutting sample was obtained to determine the presence of geological zones along the borehole that are likely to possess producible hydrocarbons. In one embodiment the degree of lightness is in the range of 50 to 52 ($L^*$ value) for samples having a greater likelihood of possessing producible hydrocarbons. The gathered $L^*$ data may also be combined with other well logging data to improve the accuracy of the hydrocarbon layer determinations.

A method for determining the location of a drilling bit within a hydrocarbon layer during directional drilling operations, the method steps comprising: obtaining at least one pulverized drill cutting sample at periodic intervals during the horizontal drilling process of a borehole, each drill cutting sample representative of the geological material encountered at a measured depth; measuring the pulverized drill cutting sample with a color measuring device to obtain a value representing the degree of lightness of the particular pulverized drill cutting sample; and comparing the measured lightness value with the lightness value of preceding samples to determine whether the drilling bit is located within the desired geological layer. In one embodiment the degree of lightness is in the range of 50 to 52 ($L^*$ value) for samples having a greater likelihood of possessing producible hydrocarbons. The gathered $L^*$ data may also be combined with other well logging data to improve the accuracy of the hydrocarbon layer determinations.

BRIEF DESCRIPTION OF THE SEVERAL VIEWS OF THE DRAWING(S)

The present invention will be more fully understood by reference to the following detailed description of the preferred embodiments of the present invention when read in conjunction with the accompanying drawings, wherein.

Figure 1:
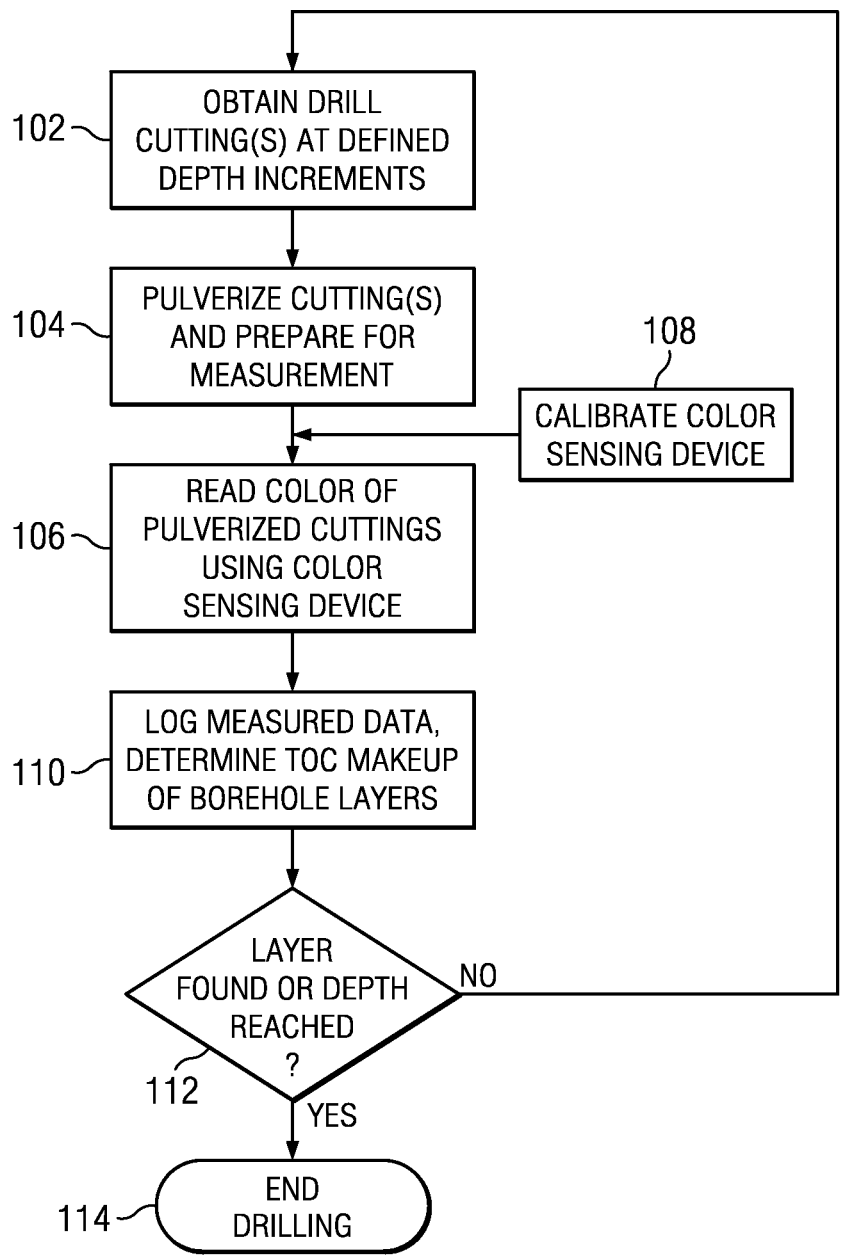
FIG. 1 is a flow diagram representing the steps of the present invention

The above figures are provided for the purpose of illustration and description only, and are not intended to define the limits of the disclosed invention. Use of the same reference number in multiple figures is intended to designate the same or similar parts. Furthermore, when the terms "top," "bottom," "first," "second," "upper," "lower," "height," "width,"

"length," "end," "side," "horizontal," "vertical," and similar terms are used herein, it should be understood that these terms have reference only to the structure shown in the drawing and are utilized only to facilitate describing the particular embodiment. The extension of the figures with respect to number, position, relationship, and dimensions of the parts to form the preferred embodiment will be explained or will be within the skill of the art after the following teachings of the present invention have been read and understood. (58,266).

DETAILED DESCRIPTION OF THE INVENTION

FIG. 1 presents a flow diagram representing the steps of the present invention. As shown, the method begin by obtaining drill cuttings at defined depth increments along a borehole (102). The drill cuttings are gathered and cleaned for further processing, by an individual with access to the drilling equipment during drilling operation. For example, with a typical well borehole, a mud logger is employed to take detailed records of the borehole as it is drilled. The mud logger enters the borehole data in a file log such as the industry standard LAS format, recording such data in ten foot depth increments along the borehole. In addition to these traditional well logging duties, the mud logger may also collect, log, and clean drill cuttings samples at each of these increments in preparation for use in the instant invention. While logging in ten foot increments is discussed, it is possible to decrease the depth interval to obtain additional data points which will increase the overall resolution of the borehole data.

Once the cutting samples are gathered, logged, and cleaned, they are pulverized and placed into a Petri dish (104) or other suitable container. In the present invention, it is preferable that the Petri dish or container be of optical or near-optical quality to improve the accuracy of color measurements. However, other quality grades of container may be utilized if the clarity is considered during measurements.

Ideally each Petri dish that is utilized should have approximately the same optical or near-optical quality so that variations between each dish do not significantly affect the L* value of the respective cutting sample. However, it is possible to utilize Petri dishes having varying degrees of optical transmissivity by measuring and utilizing this property in determination of the L* values for a given set of samples.

In the present embodiment approximately 5 to 7 grams of drill cuttings from each sample are pulverized using a grinding or crushing device (for example, a mortar and pestle, roll crusher or similar device, whether automated or manual) to achieve a particle size of approximately 4 microns. Decreasing the particle size reduces dispersion of the reflections of light from the material and improves the overall light reading of the cuttings. For example, when raw cuttings are placed in a container for measurement, a coarse particle size (i.e., not pulverized) presents the measurement device with particle facets that tend to skew lightness or color measurements due to the light reflecting from the facet such that it is not detected by the color measurement device. By providing pulverized particles, the measurement device is presented with a greater amount of cutting surface area and, consequently, a more uniform color distribution from which to obtain a measurement. One of ordinary skill will appreciate that t is possible to utilize an even smaller particle size than 4 microns. However, a point of diminishing returns is reached for the increased sample preparation efforts.

Figure 2:
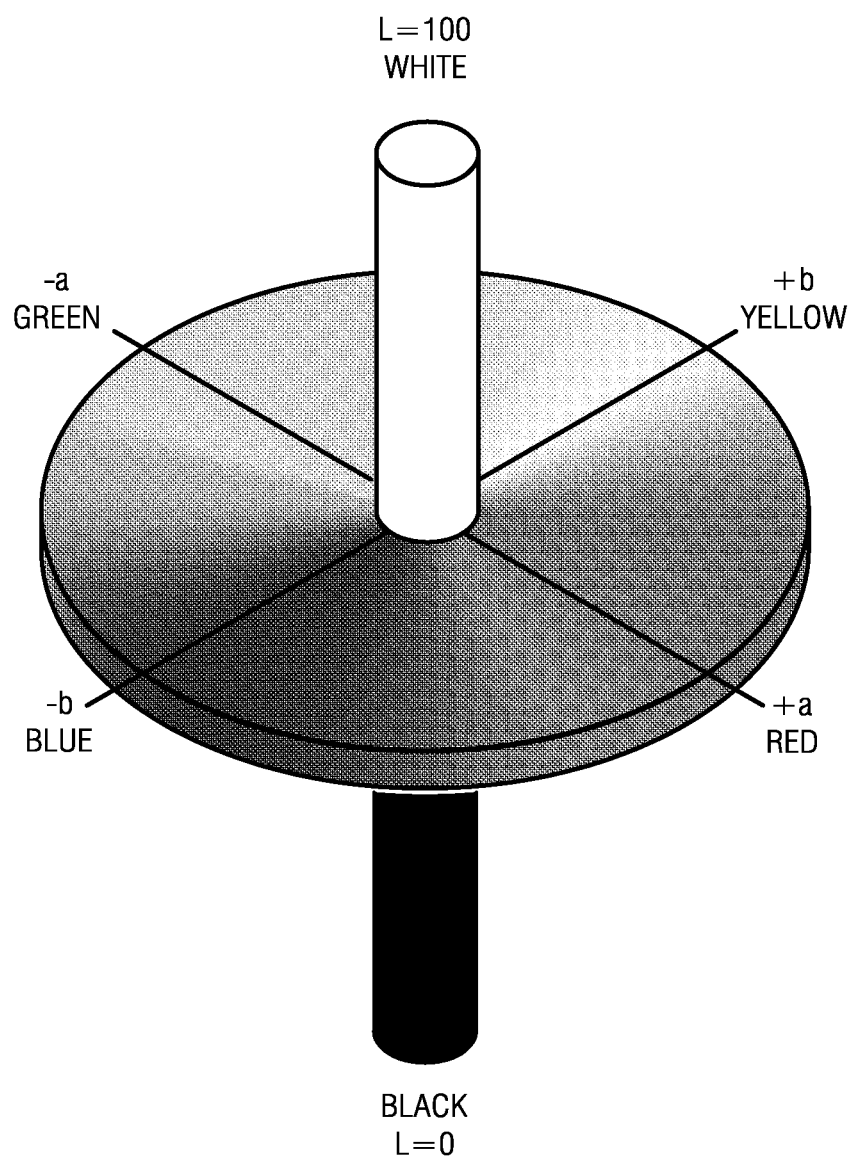
FIG. 2 is an graphical depiction of an $L^*a^*b^*$ color space representation.

Once the drill cutting samples are properly prepared, a color measuring device is utilized to read the cutting sample's color components (106). In this embodiment, a color measuring device is utilized that provides output representing the L*a*b* color space. The L*a*b* color space (also referred to as CIELAB) is one of the more popular color spaces for measuring color. Referring to FIG. 2, in this color space, L* indicates lightness and a* and b* are the chromaticity coordinates. In another embodiment, the measuring device uses the L*C*h color space, wherein L* represents lightness; C* represents chroma; and h is the hue angle. In either color space, L* is a value ranging from 0 (dark, i.e., black) to 100 (light, i.e., white).

The color measuring device in this embodiment is the Konica Minolta Chroma Meter CR-400 colorimeter. This device was selected based upon its accuracy, ease of use, relatively low cost, and durability for obtaining repeatable measurements without undue setup time. Also, this colorimeter has the capability of relatively simple setup and calibration using a gray calibration tile to ensure repeatability of sample measurements across different colorimeters. Although the present embodiment utilizes the CR-400 colorimeter, one of ordinary skill will understand that other devices capable of measuring color and lightness and generating an L* value are contemplated and are within the scope of the invention. For example, it is possible to utilize a spectrophotometer such as the Konica Minolta CM-3700d or similar device, however, such devices tend to be more costly and delicate than the stated colorimeter.

Organic carbon tends to be blackish in color. Accordingly, because total organic carbon (TOC) content of shale is of significant interest with the present invention, the focus in this embodiment is on the lightness measurement of the pulverized samples. If a particular cutting sample is heavy with TOC, it will be darker than a cutting sample that has a lower TOC. Therefore, cutting samples will fall somewhere in the range between white (L*=100) and black (L*=0), which presents visually as grayscale.

Figure 3:
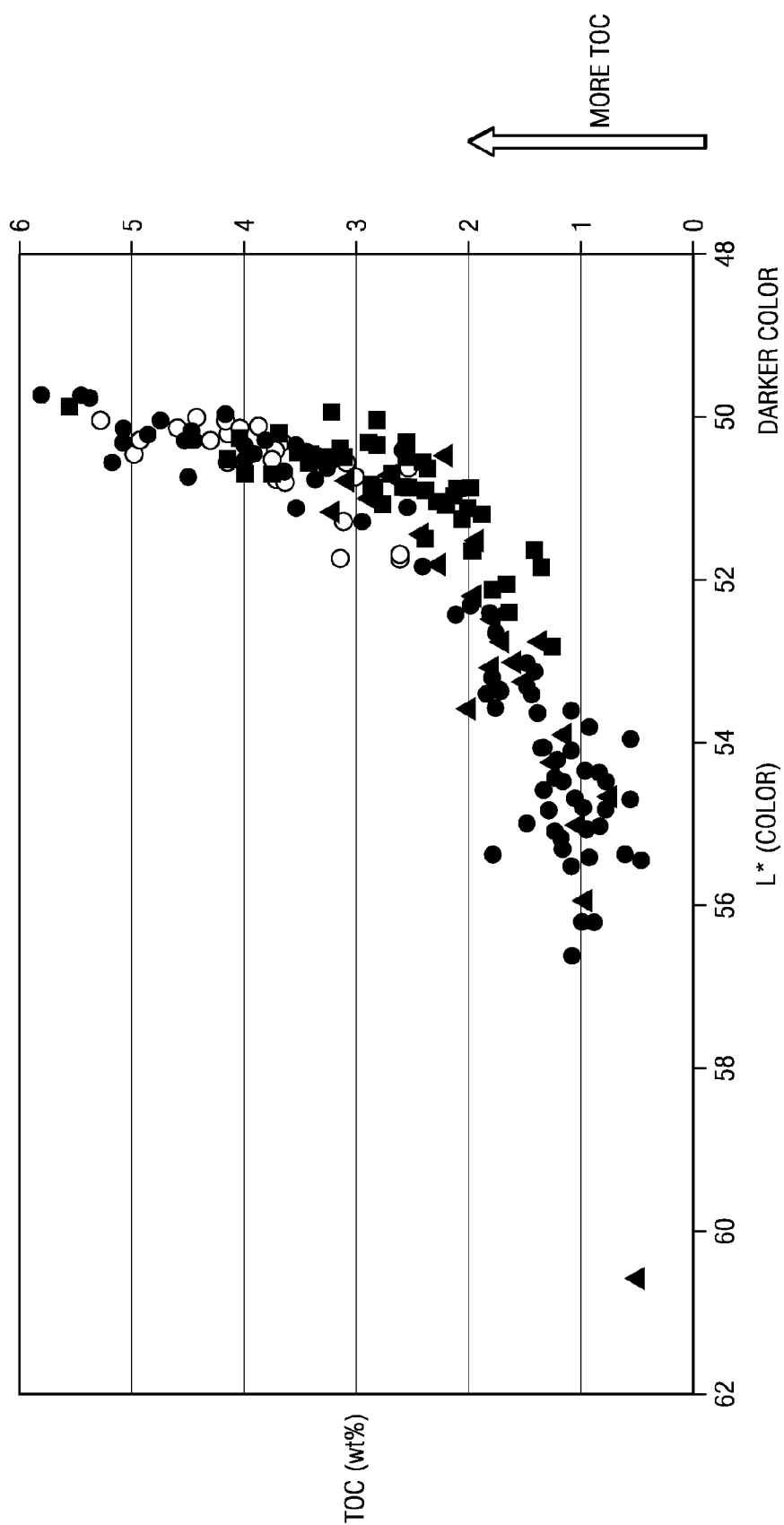
FIG. 3 is a graph of core data for a borehole, comparing the $L^*$ value with measured TOC.

Empirical evidence indicates that a cutting sample with an L* value of approximately 52 or less indicates a significantly high concentration of TOC such that producible hydrocarbons may exist. Subsequent drilling in these shale zones has further validated this position. However, actual core data from producible shale also demonstrates that the lower range of L* approaches a vertical asymptote of approximately 50 as shown on the graph of FIG. 3. From the core data, increasing amounts of TOC do not significantly change the resulting grayscale color. A cutting specimen with TOC of 10% or greater has approximately the same L* value of one with a TOC of approximately 6%. FIG. 3 represents a graph of the core data, comparing the L* value with measured TOC, reflecting this finding. As such, based upon this empirical data, the present embodiment focuses attention on shale layers having an L* value of between 50 and 52. In yet another embodiment L* values of less than 52 are preferable as they indicate increasing concentrations of TOC, such as when utilizing Petri dishes higher a optical quality. For example, the present embodiment utilizes the Becton Dickinson BD Falcon Easy-Grip Bacteriological Petri Dish, which is made from polystyrene, measures approximately 35×10 mm and, according to the manufacturer, provides "flat, distortion free optics." One of ordinary skill in the art will appreciate that other similar Petri dishes may be utilized and are within the scope of the present invention.

Borehole measurements are commonly taken during or after drilling. For example, during drilling, the drilling bit may be accompanied down the borehole by various tools having sensors that measure various features of the borehole, such as density, porosity, resistivity, formation pressures, gamma-ray values, etc. The electrical characteristics of the borehole are recorded in an electric log (or E-log as commonly known) while borehole gamma measurements are recorded in a Gamma-log. Ultimately, this data is added to the well LAS file log. Given that this data is also logged at predefined depth increments, along with the cutting samples that are obtained and measured, it is possible to make direct comparisons of the well log data with the measured lightness values of the drill cuttings. In doing this, it is possible to recognize trends and to further improve the statistical accuracy of the hydrocarbon layer determination.

Figure 4:
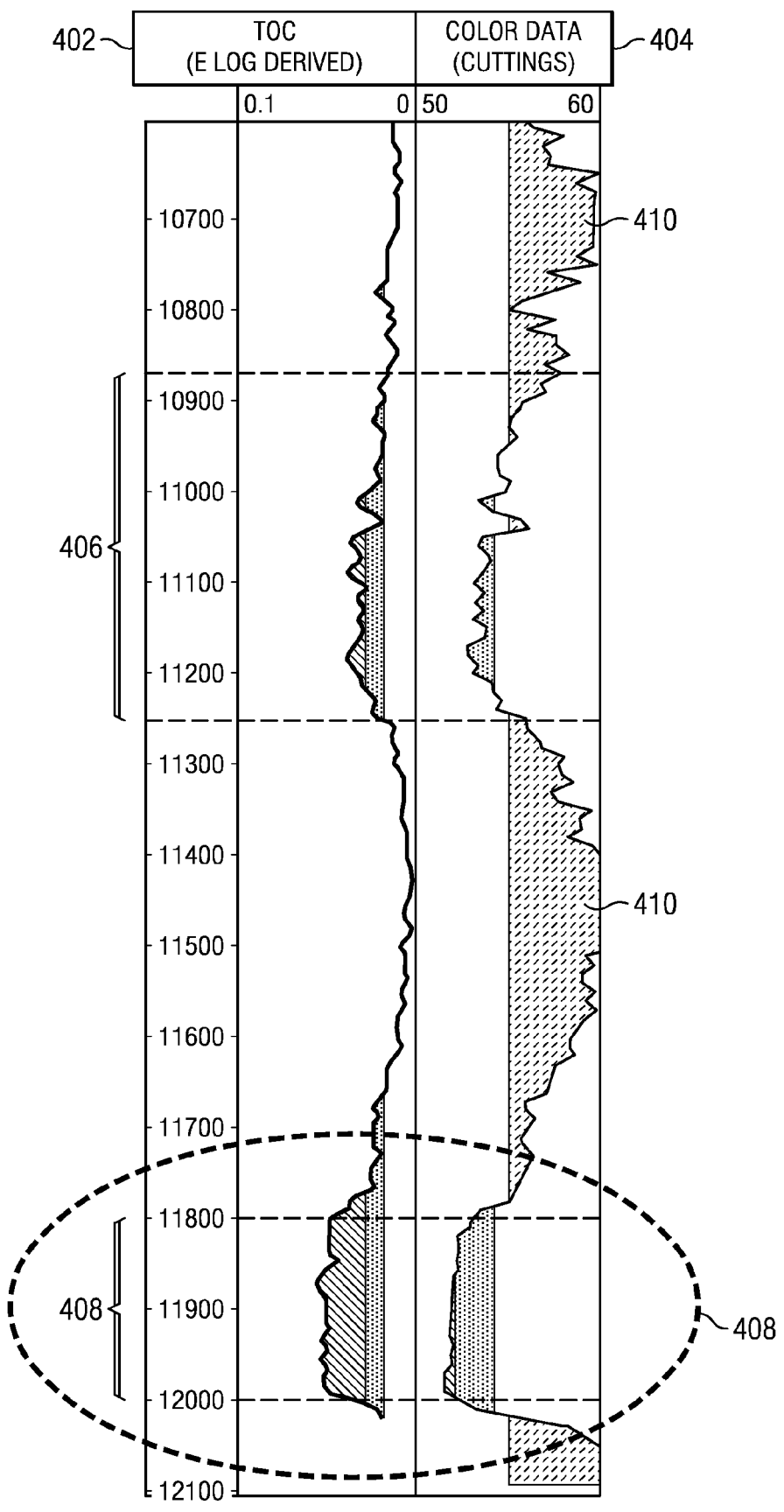
FIG. 4 is a graph comparing the TOC of the layers of a borehole as determined from the electric log data and the $L^*$ data.

Referring again to FIG. 1, as the cutting samples are measured, the resulting lightness values are accumulated and recorded in conjunction with the depth at which the sample was obtained (110). This L* data may also be combined with any E-log data or Gamma-log present in the well log. Once the measurements are complete, it is possible to graph the resulting data to obtain a visual representation of the TOC content of the shale layers. FIG. 4 depicts such a representation. As shown in this figure, the E-log derived TOC data (402) is presented alongside the color data (L* value data) (404) obtained from the cutting samples for a single borehole. The graphs show a direct correlation between a relatively high TOC value and an L* value of approximately 52. In this borehole a first and second hydrocarbon layer (406 and 408, respectively) were located at defined depth intervals. Subsequent core testing determined that these two layers (406 and 408) contained producible hydrocarbons, validating the measured results. Shale layers with negligible TOC are indicated by L* values of greater than 52 (410).

In addition to its correlation with TOC, the correlation between L* color values and shale layer permeability and porosity has also been determined. In another embodiment, the L* color value also provides an indication as to the permeability and the porosity of the various shale layers within a borehole. Using the L* values, as before, an L* value of approximately 52 represents a shale hydrocarbon layer of desirable permeability and porosity, indicating that there is a high likelihood of producible hydrocarbons. L* values greater than 52 indicate declining permeability and porosity of the layers, indicating that there is a low likelihood of producible hydrocarbons.

Based upon the graph of FIG. 4 it is possible for a driller to accurately set his well depth to those areas of high TOC (406 or 408). Although electric logging data is quite common, it is also quite expensive. Also, certain geological conditions can place undue stresses on the measurement equipment (temperature, vibration, pressures, etc.) which shortens the life of the measurement tool, increasing costs further still. A drilling bit is substantially more durable than the measurement tool. By utilizing the present invention, a drill operator need only collect the cuttings that are forced to the surface with the drilling mud in order to determine the TOC makeup of the borehole. Consequently, costly measurement tools are not necessary and need not be sacrificed to obtain costly data.

Directional drilling is commonly utilized to drill horizontal (or lateral) boreholes through a particular shale layer to increase well output. Such an evolution is costly and fraught with risks given the fact that drill bit location must be estimated. The present invention removes some of the guess work from this equation by allowing the driller to readily locate the hydrocarbon layer of interest, determine the kick-off point from the data, and drill horizontally into the hydrocarbon layer. As the drill bit progresses along the hydrocarbon layer, the mud logger continues to collect, clean, and log drill cutting samples at regular depth intervals (for example, every 30 feet). As the bit progresses, the samples may be pulverized and measured with the color sensing device to obtain an L* value. In this fashion, each L* value may be compared with the previous L* values experienced in the hydrocarbon layer to determine if the bit is still within the layer or if it has breached into an adjacent layer.

Referring again to FIG. 1, it is recommended that the color sensing device be calibrated from time to time (108) to ensure repeatability of data. Calibration is often necessary if different color sensing devices are utilized (differences between machines) or if a color sensing device is being used for the first time or after extended periods of inactivity. Calibration is necessary given the fact that the desired L* range for TOC is rather narrow. To calibrate, a grey calibration tile of a known L* a* b* measure is utilized because such a calibration device is similar to the cutting samples the device is intended to measure. Finally, once the appropriate shale layer or borehole depth is reached (112), drilling ends (114).

The invention may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes which come within the meaning and range of equivalency of the claims are therefore intended to be embraced therein. Further, the recitation of method steps does not denote a particular sequence for execution of the steps. Such method steps may therefore be performed in a sequence other than that recited unless the particular claim expressly states otherwise.

We claim:

1. A method for detecting hydrocarbon zones in a geological formation, the method steps comprising:
    obtaining a plurality of pulverized drill cutting samples, each drill cutting sample comprising geological material representative of the geological material encountered at a measured depth of a borehole, with each drill cutting having been obtained at periodic intervals during a drilling process;
    measuring each pulverized drill cutting sample with a color measuring device to obtain a value representing a degree of lightness of the particular pulverized drill cutting sample; and
    analyzing the measured lightness values in relation to borehole depth at which each pulverized drill cutting sample was obtained to determine the presence of geological zones along the borehole that are likely to possess producible hydrocarbons.

2. The method of claim 1, wherein the color measuring device output includes an L* color space value, the method steps further including:
    denoting samples having an L* value in a range of 50 to 52 as having a greater likelihood of possessing producible hydrocarbons.

3. The method of claim 1, wherein the color measuring device output includes L*a*b* color space values.

4. The method of claim 1, wherein the color measuring device output includes L*a*b* color space values, the method steps further comprising:
    measuring each pulverized drill cutting sample with a color measuring device to obtain values representing a chromaticity of the particular pulverized drill cutting sample; and
    analyzing the measured lightness values and chromaticity values in relation to the borehole depth at which each pulverized drill cutting sample was obtained to determine the presence of borehole zones that are likely to possess producible hydrocarbons.

5. The method of claim 1, wherein the drill cutting particles have a particle size of less than approximately 4 microns.

6. The method of claim 1 wherein an optical-quality Petri dish contains the pulverized drill cutting samples for measurement.

7. The method of claim 1, the method steps further comprising:
correlating measured lightness value data with electric well logging data to determine the presence of hydrocarbon zones along the borehole depth.

8. The method of claim 1, the method steps further comprising:
correlating measured lightness value data with gamma-ray logging data to determine the presence of hydrocarbon zones along the borehole depth.

9. A method for determining the location of a drilling bit within a hydrocarbon layer during directional drilling operations, the method steps comprising:
obtaining at least one pulverized drill cutting sample at periodic intervals during a horizontal drilling process of a borehole, the at least one drill cutting sample comprising geological material representative of the geological material encountered at a measured depth;
measuring the pulverized drill cutting sample with a color measuring device to obtain a value representing a degree of lightness of the particular pulverized drill cutting sample; and
comparing the measured lightness value with the lightness value of preceding samples to determine whether the drilling bit is located within a desired geological layer.

10. The method of claim 9, wherein the color measuring device output includes L*a*b* color space values.

11. The method of claim 9, wherein the color measuring device output includes L*a*b* color space values, the method steps further comprising:
measuring each pulverized drill cutting sample with a color measuring device to obtain values representing a chromaticity of the particular pulverized drill cutting sample; and
analyzing the measured lightness values and chromaticity values by order of borehole depth that the respective pulverized drill cutting sample was obtained to determine the presence of borehole zones that are likely to possess producible hydrocarbons.

12. The method of claim 9, wherein the drill cutting particles have a particle size of less than approximately 4 microns.

13. The method of claim 9 wherein an optical-quality Petri dish contains the pulverized drill cutting samples for measurement.

14. The method of claim 9, the method steps further comprising:
correlating measured lightness value data with electric well logging data to determine whether the drilling bit is within the desired geological layer.

15. The method of claim 9, the method steps further comprising:
correlating measured lightness value data with gamma-ray logging data to determine whether the drilling bit is within the desired geological layer.

\* \* \* \* \*